United States Patent [19]
White

[11] Patent Number: 5,952,578
[45] Date of Patent: *Sep. 14, 1999

[54] ULTRASONIC EXAMINATION OF COATED PARTS

[75] Inventor: Dennis A. White, St. George Island, Fla.

[73] Assignee: Beloit Technoloiges, Inc., Wilmington, Del.

[*] Notice: This patent is subject to a terminal disclaimer.

[21] Appl. No.: 09/093,146

[22] Filed: Jun. 8, 1998

Related U.S. Application Data

[63] Continuation-in-part of application No. 08/948,959, Oct. 10, 1997, which is a continuation-in-part of application No. 08/690,763, Aug. 1, 1996, Pat. No. 5,681,996.

[51] Int. Cl.[6] ............................. G01N 29/06; G01N 29/10
[52] U.S. Cl. ................................. 73/622; 73/629; 73/634
[58] Field of Search ........................... 73/597, 598, 600, 73/599, 622, 629, 618, 104, 105, 634

[56] References Cited

U.S. PATENT DOCUMENTS

| | | | |
|---|---|---|---|
| 4,398,421 | 8/1983 | White | 73/597 |
| 4,586,379 | 5/1986 | Burkhardt, Jr. | 73/622 |
| 4,679,437 | 7/1987 | Koike et al. | 73/622 |
| 5,329,561 | 7/1994 | Desruelles | 73/588 |
| 5,349,860 | 9/1994 | Nakano et al. | 73/597 |
| 5,681,996 | 10/1997 | White | 73/626 |

*Primary Examiner*—Hezron Williams
*Assistant Examiner*—Helen C. Kwok
*Attorney, Agent, or Firm*—Lathrop & Clark LLP

[57] ABSTRACT

When an ultrasonic transducer for detecting discontinuities and/or delaminations in a thin layer of coated material applied to a metal plate or the outside wall or surface of a cast iron dryer cylinder is directed at the coated surface to be inspected at a particular angle, about 10 percent of the single will appear as Harris waves which propagate into the coated test plate at 90 degrees to the surface. This signal which propagates vertically is polarized, with the result that the signal has a greatly improved signal-to-noise ratio. For incident medium of Lucite and employing shear wave refracting in the medium of Lucite, the specific angle is approximately 66 degrees from the vertical for best signal-to-noise ratio. Shear or longitudinal waves can be employed to affect the detection of subsurface defects with the particular angle changing depending on the relation of the velocity of the sound waves in the refracting medium to the velocity of sound waves in the incident medium.

22 Claims, 4 Drawing Sheets

ULTRASONIC EXAMINATION OF COATED PARTS

RELATED APPLICATIONS

This application is a continuation-in-part of U.S. patent application Ser. No. 08/948,959, filed Oct. 10, 1997, which is a continuation-in-part of U.S. patent application Ser. No. 08/690,763, filed Aug. 1, 1996 which is now U.S. Pat. No. 5,681,996 issued on Oct. 28, 1997.

BACKGROUND OF THE INVENTION

FIELD OF THE INVENTION

In the manufacture of tissue paper and paper towel a web of paper fibers is formed and pressed against a Yankee dryer. After drying, the web is scraped from the surface of the Yankee dryer, giving the web a creped texture which gives the paper it's soft absorptive characteristics. Because only a single dryer is used the Yankee dryer is normally large, typically from twelve to twenty-five feet in diameter. Moreover, the Yankee dryer is heated by steam at pressures of up to 160 psig. A Yankee dryer may be 400 inches long and may have a total weight of over 100 tons. Because of its large size and high operating pressure, a Yankee dryer typically has a cylinder wall thickness of over two inches. Yankee dryers are generally formed from cast iron; a material which has good release characteristics if the surface is properly ground. Thus, the surface of a Yankee dryer requires periodic regrinding to maintain the proper surface finish.

A Yankee dryer is a pressure vessel and the safety precautions typically employed with any pressure vessel or boiler must be observed. In U.S. Pat. No. 4,398,421 an apparatus for measuring the thickness of a work piece which is useful for measuring the thickness of steam boiler walls is disclosed. Determining the wall thickness of a Yankee dryer is useful but it is also desirable to detect small voids within the thickness of the dryer wall.

Existing ultrasonic inspection systems have a limited capability for detecting small voids or finding voids near the surface of cast iron parts. Ultrasonic signals in cast iron are scattered and reflected from grain boundaries present in the cast iron. This characteristic of cast iron makes detecting small discontinuities very difficult. Even measurement of thickness in cast iron can be difficult to perform. One national study has found errors of over 40 percent in thickness measurements of cast iron with some conventional techniques. Ultrasonic transducers typically have an interface zone of up to one-half inch where subsurface discontinuities can not be detected.

X-ray methods are used for the inspection of Yankee dryer rolls. X-ray methods, however, require the use of radioactive sources which are cumbersome and dangerous. In practice, x-ray images are only made of limited portions of the Yankee dryer. Furthermore, x-ray imaging is not effective at detecting hair-line cracks because such cracks do not significantly reduce the density of the material. Hair-line cracks are, however, typically detectable by ultrasonics.

In U.S. application Ser. No. 08/690,763 filed Aug. 1, 1996, now U. S. Pat. No. 5,681,996, which is incorporated herein by reference, a method of ultrasonic inspection was disclosed which is capable of detecting flaws in a Yankee dryer with a high signal-to-noise ratio.

In U.S. Pat. No. 5,681,996 it was disclosed that if an ultrasonic signal is directed at a surface to be inspected at a particular angle, about ten percent of the signal will appear as Harris waves which propagate into the test plate at ninety degrees to the surface. The signal which propagates vertically is polarized, with the result that the signal detects flaws with greatly improved signal-to-noise ratio. The particular angle is between that angle where the ultrasonic signal is refracted so as to propagate parallel to the surface of the metal plate and that angle where the ultrasonic signal is reflected by the test plate. Employing shear waves, for an incident medium of water and a refracting medium of cast iron, the specific angle is approximately 33 degrees from the vertical. For steel the specific angle is approximately 31 degrees. For brass the angle is about 50 degrees.

This particular angle while detecting flaws, produced a signal without an apparent time of flight—meaning that the depth of the flaw could not be determined with the disclosed method. Methods of finding the depth of a flaw using ultrasonic energy can be difficult to calibrate. Traditional methods require a flat bottomed hole drilled from a surface opposite the surface from which the ultrasonic interrogation is conducted. A hole with a flat bottom is difficult to drill and difficult to precisely line up parallel to the interrogation surface.

In U.S. application Ser. No. 08/948,959, filed Oct. 10, 1997, which is incorporated herein by reference, a method of ultrasonic inspection was disclosed which is capable of determining the depth of any detected flaw in a Yankee dryer.

In the '959 application, an ultrasonic inspection method and apparatus based on a calibration method and an empirically observed interrogation angle was described. An inspection method for a cast iron dryer shell which can reliably detect discontinuities and their locations within the casting was described. The U.S. Pat. No. 5,681,996 patent and the Ser. No. 08/948,959 application relate to ultrasonic instruments for nondestructive testing of materials in general and for nondestructuring testing of large cast cylinders in particular. The invention of the subject application is related to the ultrasonic interrogation of coated materials in general and for nondestructive testing of coated, large cast cylinders in particular.

The outside shell or surface of paper and tissue machine cast iron dryer cylinders becomes worn in service due to abrasion during operation. The primary cause of wear to the outside shell of a paper machine dryer cylinder is attributable to a doctor blade.

A doctor blade is generally brought into intimate contact with the outside shell or surface of a dryer cylinder in order to scrape or crepe off the web of paper or tissue traveling over the dryer cylinder.

Outside diameter shell or surface wear to a cast iron dryer cylinder adversely affects the quality of the paper or tissue product being formed. Replacing entire worn dryer cylinders is extremely costly. So that the entire dryer cylinder does not have to be replaced when the cylinder's outside shell becomes worn, the cast iron dryer cylinder outside surface is often machined or ground down until a smooth surface is obtained and a coating of metalspray is applied to the dryer cylinder surface such that the dryer cylinder is capable of further use.

There are a number of metalspray compositions capable of being used for large cast iron dryer shells generally known to those skilled in the art. Metal spray application is also generally known to those skilled in the art. Essentially, molten metal is sprayed onto the surface or outer shell of a large cast iron dryer. Typically, at the outer edges of the metalspray flame, cold splatter, known to those skilled in the art, may be deposited onto the surface of the drying cylinder. The larger the arc of the metalspray, the more cold splatter that is deposited. Cold splatter is a miniature disbond of metalspray material between the metalspray coating and the substrate upon which the coating is applied. Detectable quantities of cold splatter cause problems related to heat transfer, surface quality, and other problems as can be appreciated by those skilled in the art. Such problems compromise the quality of the tissue or paper product being formed.

Typically, during clean-out procedures of a paper or tissue machine dryer section, dryer cylinders are often exposed to water streams. Although dryer cylinders are not usually purposefully exposed to water streams, such exposure does occur. If the outside shell or surface of a dryer cylinder has been metalsprayed, there will be a difference in the coefficient of thermal expansion between the metalspray coating and the cast iron substrate. When water contacts the metalsprayed shell, the shell and metalspray begin to cool. The metalspray will cool at one rate and the cast iron dryer cylinder will cool at another rate. The difference in the thermal coefficient between the two materials can cause cracking or disbonding of the metalspray. If the metalspray is not properly adhered to the surface of the cast iron cylinder, the metalspray will likely fall or wear off at the location of the poor adherence during a paper or tissue making operation. If the metalspray wears or falls off, problems associated with poor heat transfer and surface quality will occur and a poor tissue or paper product will result.

What is needed is a method for performing complete inspection of a coated cast iron dryer cylinder for quality control and assurance of thin metalspray adhesion to cast iron dryer shells.

SUMMARY OF THE INVENTION

An ultrasonic transducer for detecting delamination and/or discontinuities in a thin layer of metalspray applied to a metal plate or the outside wall or surface of a cast iron dryer cylinder of this invention begins with the discovery that a high amplitude ultrasonic signal is generated when delaminations and/or discontinuities are detected. If no delaminations and/or discontinuities are present, no high amplitude ultrasonic signal of the metalspray is present.

An ultrasonic signal is directed at a surface to be inspected at a particular angle, about ten percent of the signal will appear as Harris waves which propagate into the coated material at 90 degrees to the coated surface. The signal which propagates vertically is polarized, with the result that the signal detects delaminations and/or discontinuities with greatly improved signal to noise ratio. The particular angle is between that angle where the ultrasonic signal is refracted so as to propagate parallel to the coated surface of the metal plate or cylinder and that angle where the ultrasonic signal is reflected by the test plate. The particular angle is measured from a normal to the coated surface of the plate being inspected and is greater than an angle covered by Snell's law:

$$\frac{\sin(\theta_1)}{V_1} = \frac{\sin(\theta_2)}{V_2}$$

$V_1$=velocity of the ultrasonic signal in a first medium
$V_2$=velocity of the ultrasonic signal in a second medium $\theta_1$=angle of incidence of the ultrasonic signal, measured from a line perpendicular to the surface of the second medium $\theta_2$=angle of refraction of the ultrasonic signal as it enters the second medium, measured from a line normal to the surface of the second medium Snell's law predicts in accord with the laws of optics, that an ultrasonic beam will be bent as it moves from a medium of lower refraction index to one of higher refraction index. In accordance with Snell's law at a selected angle of incidence of the ultrasonic signal the signal will be refracted along the surface of the material being tested. $\theta_2$ at that angle of incidence will be ninety degrees. When $\theta_2$ equals 90 degrees not all the energy of the ultrasonic signal is refracted along the surface of the material being tested. A component of about ten percent of the ultrasonic signal's power appears as a polarized signal which travels straight down from the surface and is useful for detecting flaws. This polarized or birefingent signal/beam is called a Harris wave. As the angle of incidence of the ultrasonic signal is increased the refracting signal continues to propagate along the surface of the solid until the angle of incidence is sufficiently great that the signal is totally reflected. At a selected incident angle between that required for ninety degree refraction and that required for total reflection an angle exists which produces a Harris wave which is particularly effective at detecting flaws within the surface of the coated material being tested because of a high signal-to-noise ratio that is five to twenty times larger than at normal inspection angles.

For an incident medium of Lucite and employing shear waves in the refracting medium of a metalspray coating, the specific incident beam angle is approximately 66 degrees from the vertical. Lucite is believed to be a registered trademark of E. I. Du Pont De Nemours and Company. The invention can employ shear surface waves to affect the detection of subsurface defects with the critical angle changing depending on the ratio of the velocity of the selected wave in the refracting medium to the velocity of the selected wave in the incident medium.

It is a feature of the present invention to provide a method to examine metalspray coatings for disbonds, cracks and delaminations from a cast iron substrate.

It is another feature of the present invention to provide a method for quality control of thin metalspray adhesion to cast iron dryer shells.

Further objects, features and advantages of the invention will be apparent from the following detailed description when taken in conjunction with the accompanying drawings.

DESCRIPTION OF THE PREFERRED EMBODIMENT

Figure 1:
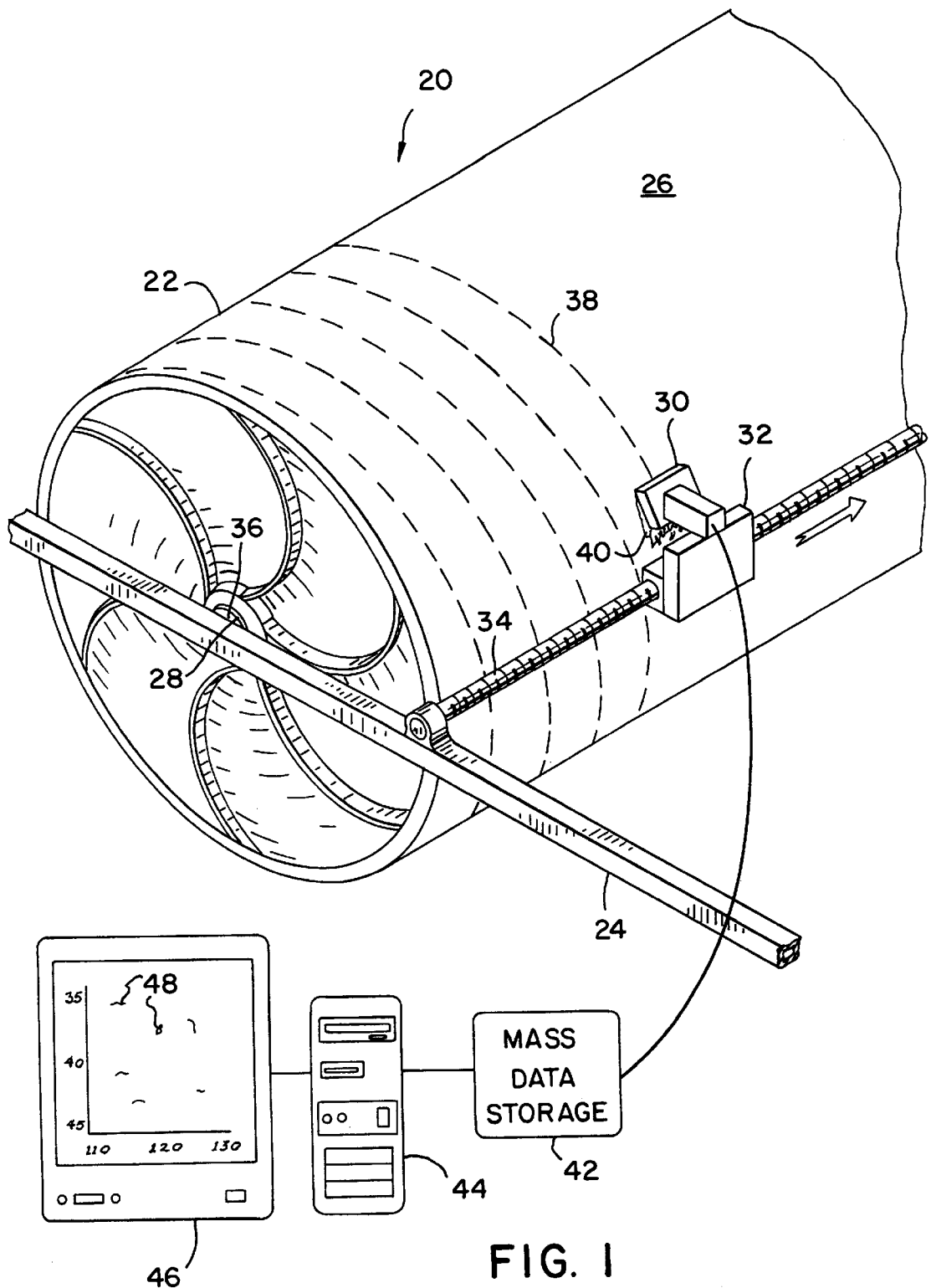
FIG. 1 is an elevational isometric view of a dryer roll sting being inspected with ultrasonic energy and the results being recorded.

Referring more particularly to FIGS. 1–7 wherein like numbers refer to similar parts an ultrasonic Yankee dryer inspection apparatus 20 is shown in FIG. 1. A Yankee dryer 22 is mounted on an inspection frame 24. The dryer 22 has a cylindrical coated surface 26 on which a tissue web is dried. The Yankee dryer 22 is mounted to a bearing 28 on the frame 24 and is caused to rotate by a drive mechanism (not shown). An ultrasonic transducer 30 is mounted to a crossfeed 32 which rides on a machine screw 34. The machine screw 34 is caused to rotate by a drive mechanism (not shown). The rotation of the machine screw 34 causes the crossfeed 32 with the ultrasonic transducer 30 mounted thereon to scan the surface 26 of the dryer 22 along a line parallel to the dryer axis 36. The combination of the rotary motion of the dryer 22 with the linear motion of the transducer 30, causes the transducer to describe a spiral pattern 38 on the surface of the Yankee dryer 22. The spiral pattern 38, as shown in FIG. 1, is shown widely spaced for illustrative purposes but is actually a tight spiral wherein the transducer advances along the surface 26 of the dryer 22 about ⅛ inches per revolution.

An incident medium 40, such as Lucite, couples the ultrasonic energy from the transducer to the coated surface of the Yankee dryer 22. It is envisioned that a coupling fluid, typically water, could be used in place of Lucite 40 such as described in U.S. Pat. No. 5,681,996, which could couple the ultrasonic energy from the transducer to the coated surface of the Yankee dryer 22. The output of the transducer is stored in digital format on a mass data storage device 42 such as a hard-disk or a DAT (Digital Audio Tape), etc. From the mass storage device 42 a computer 44 or oscilloscope (not shown) can process the data for display. A computer display 46 shows a plan view of the dryer 22 cylindrical coated surface 26 where discontinuities and/or delaminations 48 are displayed for a selected portion of the dryer coated surface 26. The computer can also be used to display the amplitude of the reflected signal for a particular location. To identify the depth and length of any detected discontinuities a separate scan using conventional techniques may be required. However, since the metalspray thickness of the dryer coated surface 26 is generally only about 0.020 inches, but may range from 0.1–0.025 inches, if a discontinuity and/or delamination is found, a profile grind of the metalsprayed surface is warranted in order to repair the affected areas. Thus, the depth or length of any discontinuity is generally not needed for this application.

Although an automated ultrasonic examination technique is described with reference to FIG. 1, a manual operation is also possible. In such a situation, the transducer 30 coupled with the Lucite medium 40 held by an operator is manually traversed over the coated surface 26. In this way, localized testing is easily controlled.

Figure 2:
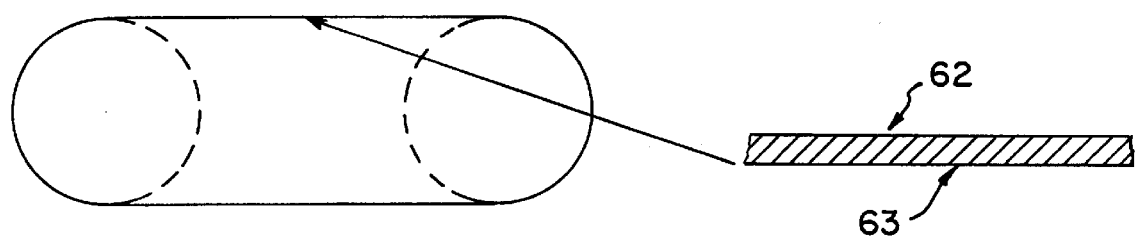
FIG. 2 is a perspective view of a dryer roll casting showing metalspray coating as applied to the cast iron outside diameter surface.

FIG. 2 shows a perspective view of a dryer roll casting. A metalspray coating surface 62 is applied to the dryer roll casting outside diameter top surface 63. The application process for metalspray and the reasons for applying a metalspray coating to a dryer roll casting are generally known to those skilled in the art as set forth in the Background section herein. The subject invention pertains to analyzing the metalspray coating once it has been applied to the dryer roll surface, to make sure the metalspray coating does not contain any deformities. A poor quality metalspray coating has significant adverse effects on the quality of paper or tissue produced on such a machine, as more fully explained hereinabove.

Figure 3:
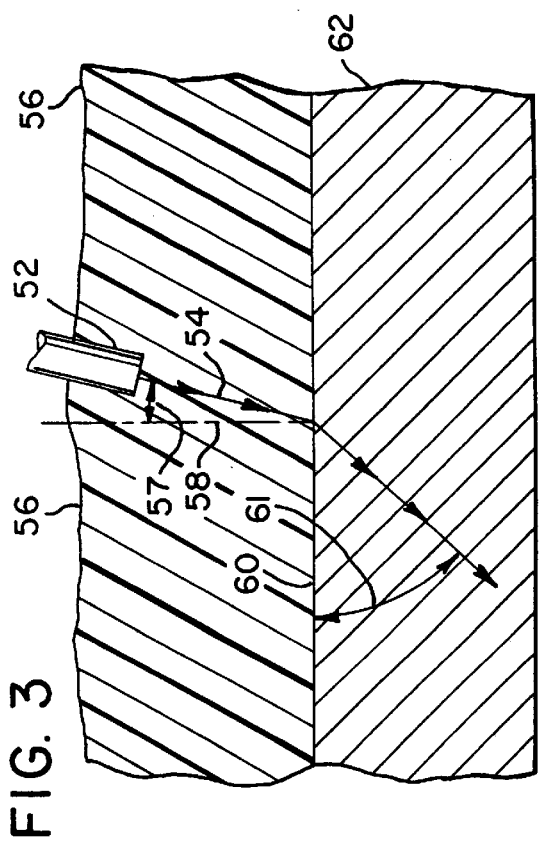
FIG. 3 is a schematic elevational view of an ultrasonic transducer projecting an ultrasonic signal through a Lucite medium into a coated material of a coated part or coated dryer cylinder.
Figure 4:
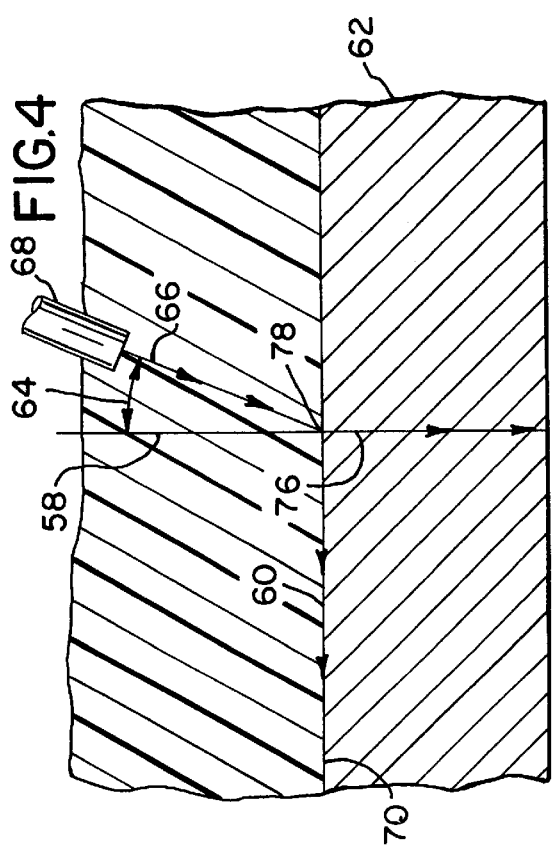
FIG. 4 is a schematic elevational view of an ultrasonic transducer projecting an ultrasonic signal at an incidence angle which causes a refracting beam to travel along the surface of a coated part or coated dryer cylinder.

FIG. 3 illustrates an ultrasonic transducer 52 projecting a beam 54 of ultrasonic energy. The ultrasonic transducer 52 intimately cooperates with a Lucite medium 56. Although transducer 52 is shown as embedded in the Lucite medium in FIGS. 3–6, it should be understood that the transducer 52 may be positioned over the top surface of the Lucite medium in an appropriate manner such as by using a transducer wedge generally known to those skilled in the art. The ultrasonic beam 54 is positioned at an angle 57 with respect to a reference line 58 normal to the surface 60 of a coated surface 62. When the ultrasonic beam 54 passes into the coated surface 62 it refracts at the coated top surface 60 at a second angle 61 in accord with Snell's law which governs the refracting of wave energy as a wave passes from a first medium to a second medium where the second medium has a higher speed of propagation for the wave energy of interest. FIG. 4 illustrates that at a selected angle 64 an ultrasonic beam 66 from the transducer 52 will be totally refracted so that the ultrasonic beam 66 will form a beam 70 which propagates parallel to the coated top surface 60 of the coated surface 62. In other words if the angle of refraction is 90 degrees so that the sine of the refracted angle is one, Snell's law may be written as:

$$\theta_1 = \arcsin(V_1/V_2)$$

V1=velocity of the ultrasonic signal in a first medium
V2=velocity of the ultrasonic signal in a second medium
θ1=angle of incidence of the ultrasonic signal, measured from a line perpendicular to the surface of the second medium When ultrasound is totally refracted at an interface between two media, Harris waves 76 are produced which originate from the point 78 where the beam 66 impinges on the coated top surface 60. The Harris waves 76 propagate vertically down into the coated surface 62 opposite the normal line 58.

Figure 5:
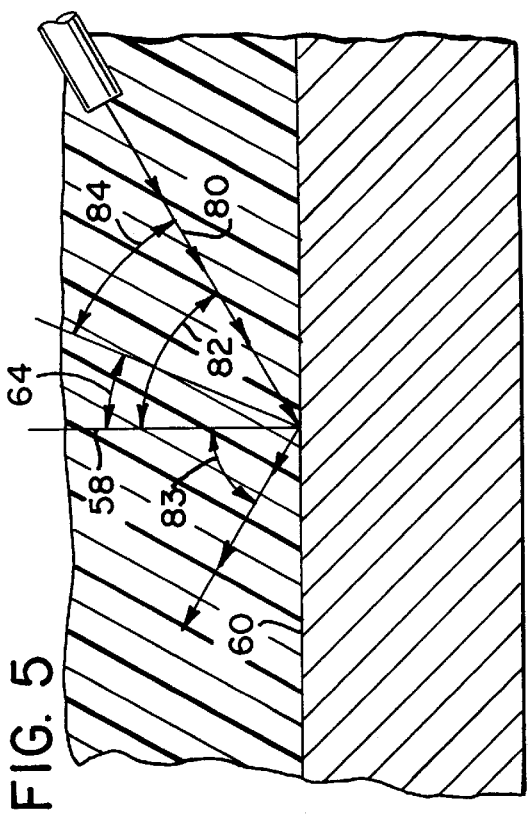
FIG. 5 is a schematic elevational view of an ultrasonic transducer projecting an ultrasonic signal at an incidence angle which causes the signal to reflect from the surface of a coated part or coated dryer cylinder.

Harris waves 76 are produced as the angle of incidence is increased from the angle 64 governed by the above equation, until as shown in FIG. 5 the ultrasonic beam 80 is totally reflected from the coated top surface 60 at angle of reflection 83. The location or measure of the total reflected angle 83 can be determined empirically by measuring when Harris waves are no longer produced as the angle between the transducer 52 and the normal line increases. Empirically the total reflection angle is about 120 percent of the selected angle 64 where Harris waves are first produced.

Figure 6:
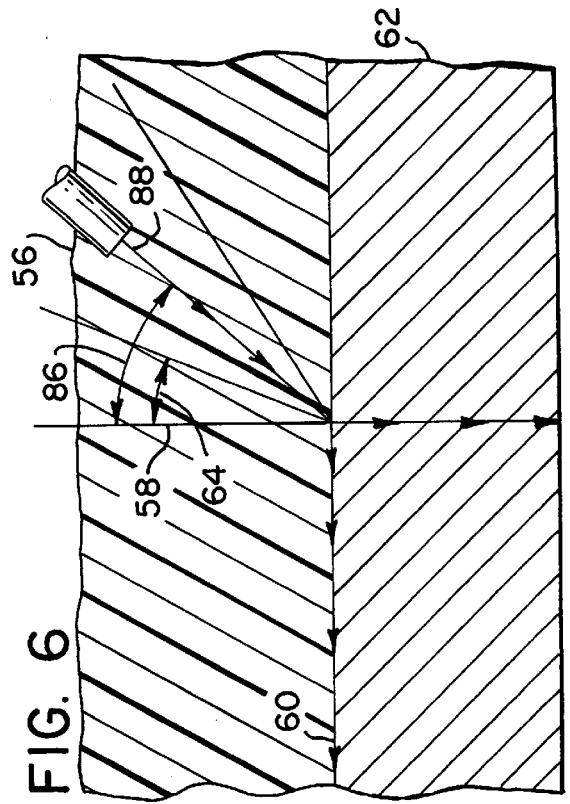
FIG. 6 is a schematic elevational front view of an ultrasonic transducer projecting an ultrasonic signal of an incidence angle of this invention which produces an ultrasonic beam which has a high signal-to-noise ratio and which penetrates normal to the surface of a coated part or coated dryer.

The arc 84 shown in FIG. 5 is between the selected angle 64 governed by Snell's law and the angle 82 where total reflection occurs. Harris waves 76 are produced within this arc 84. Within the arc 84 there is an angle 86 illustrated in FIG. 6 which has been found to have a very high signal-to-noise ratio, five to twenty times that of a typical ultrasonic interrogation beam. The signal-to-noise ratio may be at least 5, and can be 10 or higher. This angle 86, as shown in FIG. 6, allows detection of voids as small as one millimeter in coated material such as a metalspray coating which typically are difficult to inspect with conventional ultrasound techniques.

This high signal-to-noise-ratio angle 86 along which an ultrasonic beam 88 is directed, is approximately 66 degrees from the normal line 58 when the coupling medium 56 is Lucite and the coated surface 62 is a typical metalspray coating.

The optimal angle depends on the velocity of sound in the coated material 62. Sound has three wave components in a coated metalsprayed surface: an S or shear wave, an L or longitudinal wave, and surface wave. The velocity of sound differs for each type of sound wave and therefore the optimal angle will depend on the type of wave being utilized. While shear waves may have practical advantages, longitudinal waves can be used. As dictated by the above equations the angle where a beam of longitudinal waves are refracted to the surface of $V_2$ and propagate along the surface of the coated plate and also generate Harris waves is about 66 degrees from the normal line 58.

Figure 7:
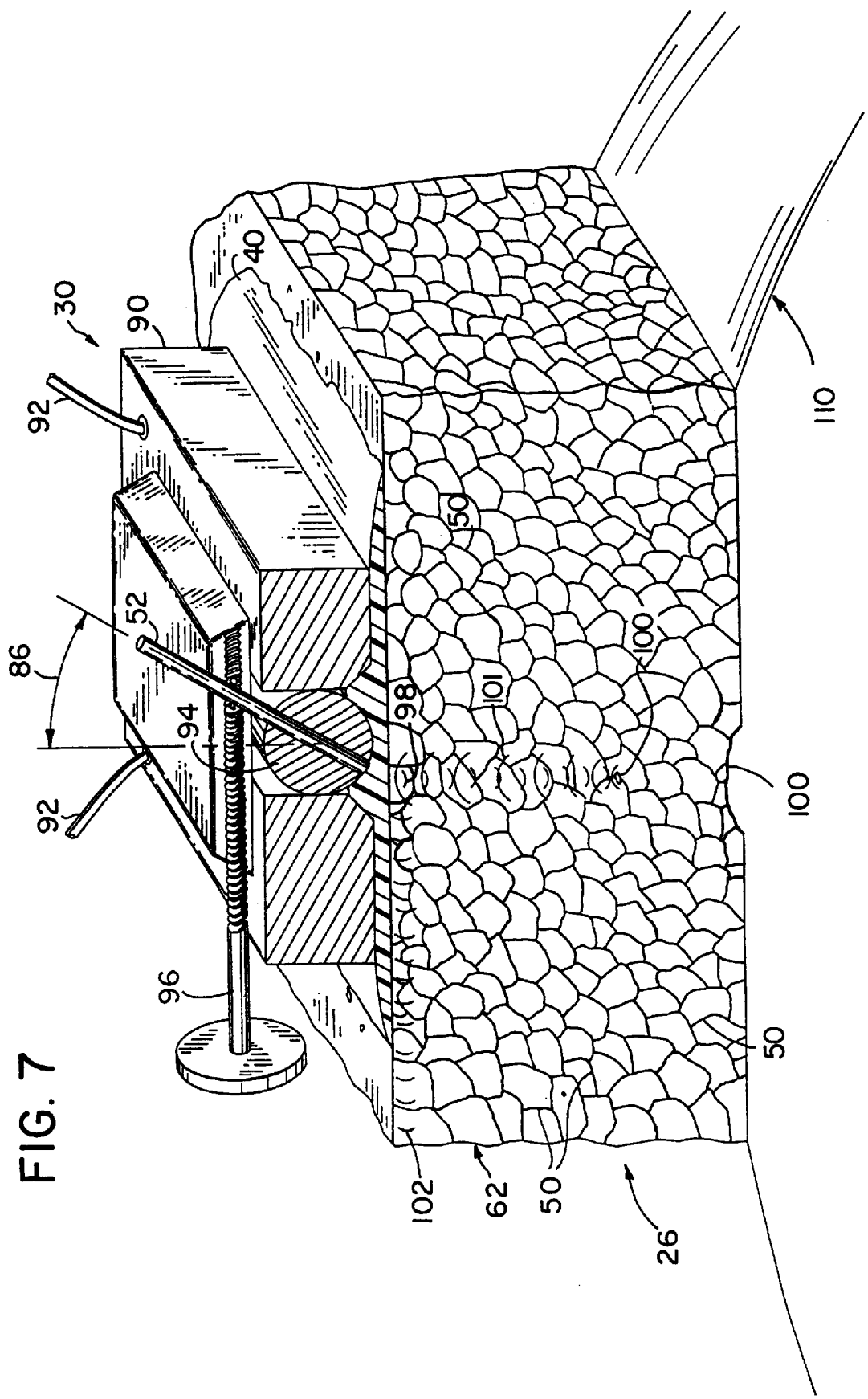
FIG. 7 is a front elevational axonometric view of an apparatus for detecting delaminations and/or discontinuities in the metalspray coating applied to a dryer cylinder or more particularly, a Yankee dryer cylinder.

The ultrasonic transducer 30 used to inspect the coated surface 62 of a Yankee dryer 22 is shown in FIG. 7. The transducer 30 employs an ultrasonic transducer 52 mounted on a carriage block 90. The carriage block 90 has ports 92 through which water or other coupling media can be supplied, if desired, as discussed in U.S. Pat. No. 5,681,996, between the carriage block 90 and the coated surface 26 of a Yankee dryer 22. As shown in FIG. 7, the carriage block cooperates with a Lucite medium 40. The ultrasonic transducer 52 is mounted in a cylinder 94 so that the angle between the transducer and the surface 26 may be adjusted. A threaded adjustment screw 96 is pivotally mounted by a universal joint which allows the screw 96 to rotate with respect to the cylinder 94. Rotation of the screw causes the angle between the transducer 52 and the surface 26 to change. It should be noted that the ultrasonic transducer of U.S. application Ser. No. 08/948,959 could be used in place of the ultrasonic transducer 30. It should also be noted that the ultrasonic transducer 52 can be fixedly attached to a simple transducer wedge, generally known to those skilled in the art, and manually maneuvered over the material being tested as further described herein.

FIG. 7 illustrates how small droplets 50 of molten metal band together as a metalspray coating is cured. When the molten droplets do not properly bond together or cold splatter occurs, or delaminations develop between the metalspray coating 62 and cast iron substrate 110, voids 100 are formed. FIG. 7 illustrates the way ultrasonic waves 98 penetrate into the coated surface 62 of a Yankee dryer 22 and are reflected 101 off small voids 100 in the depth of the coated material or at the connection point of the metalspray coating and cast iron substrate. Also illustrated are the ultrasonic waves 102 refracted along the coated top surface 60. Returns from the surface waves 1 02 can be used to detect coated surface roughness which is also an important characteristic of the Yankee dryer 30 coated surface 26.

The ultrasonic beam or waves which penetrate 90 degrees to the surface of the Yankee dryer appear from tests conducted to be polarized, as it appears that the polarized Harris waves are effective at reducing detected scatter. Nevertheless, the exact reasons why the optimal angle has a uniquely high signal-to-noise ratio is empirically observed and is not limited to the suggested mechanism. Ultrasonic energy over a wide range has been used for ultrasonic testing upon other materials and ultrasonic frequencies of 1 to 10 MHz in particular have been found to be effective.

As noted in the Background section hereof, the outside shell of paper and tissue machine cast iron dryers becomes worn in service due to abrasion during operation. As mentioned, the primary unit causing shell wear is a doctor blade. Those skilled in the art recognize that detrimental shell wear affects the quality of a paper/tissue product being produced. As a result, periodically, the cast iron surface of a used dryer cylinder is machined or ground smooth, and a metalspray is applied to the surface to rehabilitate the worn cast iron surface so that the dryer cylinder is capable of further use. Metal spray thickness of about 0.020 inches is deposited on the cast iron surfaces. A poor metalspray application will result in all the problems set forth previously hereinabove.

The method according to the present invention can quickly demonstrate the quality of a metalspray adhesion.

Immediately after a metalspray process, and subsequent cooling, the metalspray may be evaluated for quality control purposes. The method according to the present invention will detect voids in the metalspray coatings and/or areas of cold splatter, or miniature disbonds of the metalspray material after the metalspray has been applied. Detectable quantities of cold splatter should be corrected in order to prevent the quality of the tissue or paper being formed from being compromised. Poor areas of metalspray application should be profiled down and the metalspray should be reapplied.

The method according to the present invention can also demonstrate the quality of the metalspray after a dryer cylinder has been in use for some time. In operation, hot dryers are exposed to water streams when dryer sections are cleaned out and paper wads, known to those skilled in the art, are removed. Usually, these water sprays are not intended to contact dryer surfaces, but such occurrences do happen. If the shell of the dryer cylinder is metalsprayed, there will be a difference in coefficient of thermal expansion between the metalsprayed surface and the cast iron substrate. When water contacts the dryer cylinder, the cylinder begins to cool, the metalsprayed coated surface at one rate and the cast iron substrate at another. This thermal difference can cause cracking or disbonding of the metalsprayed coated surface. Other possible methods of destruction to a metalsprayed surface include the wear caused by a doctor blade or when a material object of any kind travels through a nip between a coated Yankee dryer cylinder and a pressure roll. Thus, periodic testing of the coated surface can determine if the metalspray is adequately performing.

The method of detection according to the present invention uses one transducer from one side of a cast iron metalsprayed dryer cylinder. A calibration reference standard to assist in determining depth of a flaw is not necessary, but may be used. Detection of delaminations/discontinuities in a thin layer of metalspray generates a high amplitude ultrasonic signal. If no delaminations/discontinuities are present, no high amplitude ultrasonic signals are present.

Adhesion at the interface between the coated surface and the cast iron substrate will not transmit a large UT signal with the beam according to the present invention because there is good impedance between the two materials and no interfaces to reflect sound, as a void or delamination would. Lack of adhesion will cause a large noticeable signal.

As those skilled in the art will appreciate, metalspray is typically applied to a roll surface in the following manner. The dryer cylinder to receive a coating is mounted to a bearing on a frame and is caused to rotate by a drive mechanism. A metalspray coating apparatus is typically mounted to a crossfeed mechanism along a line parallel to the dryer axis. As a dryer cylinder is rotated, the metalspray apparatus moves linearly from one end of the dryer cylinder to the other. The combination of the rotating motion of the dryer and linear motion of the metalspray apparatus causes the metalspray coating to be applied in a tight spiral pattern. When cold splatter occurs, a pattern of disbonds or defects resulting from the cold splatter can generally be observed in the spiral, circumferential path the metalspray coating travels during application to the cast iron substrate. This is important because when a defect is detected, it must be determined if the defect is cold splatter found in the metalspray or if the defect is in the substrate upon which it is applied.

For reasons not completely understood, a defect found closer to the outside surface of a piece being tested generates a higher amplitude ultrasonic signal than a defect detected further from the outside shell. Generally, it has been determined by way of the present invention that signals observed 0.3 inches from the surface of the material being tested are much higher in amplitude than those signals observed from distances greater than 0.3 inches from the outside surface.

When testing the coated metalspray, if a defect is found, the ultrasonic return signal will be extremely high because the thickness of a metalspray coating is generally only about 0.020 inches thick, much less than 0.3 inches as described above. If the return signal is not of a high amplitude, any defect found will not be within the metalspray coating.

In order to determine if the defect detected is within the coating or within approximately 0.3 inches of the substrate upon which the metalspray coating is applied, a pattern of defects should be observed.

As mentioned, cold splatter should be observed in a spiral, circumferential pattern, as this is how metalspray is applied. Thus, if a high amplitude return signal is detected and a spiral, circumferential pattern of defects is detected, cold splatter in the metalspray has been found.

It should be understood that the technique of inspecting coated parts is particularly suited for use with coated parts in the form of smooth coated plates, which term includes flat coated plates and the coated walls of large cylinders such as paper dryer rolls.

It should also be understood that the velocity of sound as used in the claims can refer to various types of components of an ultrasonic beam, and thus the angle defined by the claims will depend on whether, for example, longitudinal or shear waves are selected for measuring the speed of sound.

It should be noted that although a single transducer has been indicated for both transmitting and receiving the ultrasonic signals, alternatively, one transducer could be used to send and another to receive. In such a case the sending unit would be in the position shown, whereas the receiving unit could be in a position ranging from a sympathetic opposing angle to a normal angle.

It is understood that the invention is not limited to the particular constructions and the methods described herein. For example, it is envisioned that a new dryer cylinder could be metalspray coated prior to use and the testing of the metalspray surface could take place at such time before first use.

It is understood that the method of detecting delaminations and/or discontinuities according to the present invention may be performed in cooperation with an acoustic emission test, known to those skilled in the art.

It is understood that the invention is not limited to the particular construction and arrangement of parts herein illustrated and described, but embraces such modifying forms thereof as come within the scope of the following claims.

It should be understood that any ultrasonic transducer frequency may be used for the invention.

I claim:

1. A method of inspecting a Yankee dryer with ultrasonics, said Yankee dryer having an outside cylindrical surface, comprising the steps of:

applying a protective coating to the outside cylindrical surface of said Yankee dryer;

positioning an ultrasonic transducer over the coated surface of said Yankee dryer;

positioning an ultrasonic coupling medium between the coated surface of the Yankee dryer and the transducer;

directing a first beam of ultrasonic energy from the transducer towards the coated surface at a selected angle from a normal to the coated surface, wherein the selected angle is between an angle where the beam of ultrasonic energy travels along the coated surface and an angle where the ultrasonic energy is reflected from the surface, thereby producing a second beam of ultrasonic energy which propagates into the Yankee dryer coated surface perpendicular to the coated surface;

detecting a portion of said second beam which is reflected from a discontinuity or a delamination or a disbond in the coated surface of the Yankee dryer; and wherein the selected angle is chosen to produce a detected portion of the second beam having a signal-to-noise ratio of at least 5 to 1.

2. The method of claim 1 wherein the coupling medium is Lucite and wherein the protective coating is a metalspray coating and wherein the selected angle is about 66 degrees from the normal to the coated surface.

3. The method of claim 1 wherein the transducer is caused to traverse over the coated surface and wherein the transducer generates a signal in response to the detected portion of the second beam, and said signal is recorded for a substantial portion of the traverse of the coated surface.

4. The method of claim 3 wherein the transducer is caused to traverse the coated surface by rotating the dryer about an axis defined by the cylindrical surface and moving the transducer along the coated surface of the dryer parallel to the axis so describing a helical pattern on the cylindrical surface of the dryer.

5. The method of claim 4 wherein circumferential turns of the helical pattern are spaced about one eighth of an inch apart.

6. A method for inspecting a coated material applied to a metal plate, the method comprising the steps of:

directing a beam of ultrasonic energy through a coupling medium into a coating of the metal plate, the coating defining a surface wherein the beam propagates at a first velocity through the medium, and wherein the beam propagates at a second velocity in the coating, and wherein the coating surface defines a local normal, and wherein the beam is directed at a first angle measured from the local normal, wherein a second angle with respect to the local normal is defined as the arcsine of the first velocity of the beam through the coupling medium divided by the second velocity of the beam through the coating, and wherein a third angle is defined with respect to the local normal at which the beam is substantially reflected from the plate, and wherein an arc angle is defined between the second angle and the third angle, wherein the first angle is about the second angle plus fifty percent of the arc angle; and receiving with a transducer a reflected signal from the beam indicative of material discontinuities or delaminations or disbonds within the coating.

7. The method of claim 6 wherein the second velocity of the beam through the coating used in determining the second angle is a measure of a shear wave.

8. The method of claim 6 wherein the second velocity of the beam through the coating used in determining the second angle is a measure of a longitudinal wave.

9. The method of claim 6 wherein the coupling medium is Lucite and the coating is metalspray and the first angle is thus about 66 degrees.

10. The method of claim 6 further comprising the step of receiving a second reflected signal from a component of the beam which travels along the coated surface of the plate the second reflected signal being indicative of the coated surface roughness.

11. The method of claim 6 wherein the coated plate is part of a coated cylinder defining a roll surface of a Yankee dryer.

12. The method of claim 11 wherein the transducer is caused to traverse the roll surface by rotating the Yankee dryer about an axis defined by the cylindrical surface and moving the transducer along the coated surface of the cylinder parallel to the axis so describing a helical pattern on the cylindrical surface of the dryer.

13. The method of claim 12 wherein circumferential turns of the helical pattern are spaced about one eighth of an inch apart.

14. The method of claim 6 wherein the transducer is caused to traverse over the coated plate surface and wherein the reflected signal from the transducer is recorded for a substantial portion of the traverse of the coated surface.

15. A method of inspecting a coating of metal object having a coating surface comprising the steps of:

directing a beam of ultrasonic energy through a coupling medium into the coating at a first angle from a line normal to the coating so that a portion of the ultrasonic energy penetrates along the surface of the coating and a portion of the ultrasonic energy penetrates opposite the line normal to the coating and wherein the energy penetrating opposite the line normal to the coating is polarized;

detecting energy reflected from the portion of the energy propagating along the surface to detect the surface roughness of the object, and detecting energy reflected from the portion penetrating opposite the line normal to the coating to detect material discontinuities or delaminations or disbonds in the coating.

16. The method of claim 15 wherein the detected energy reflected from the penetrating portion is a shear wave.

17. The method of claim 15 wherein the detected energy reflected from the penetrating portion is a longitudinal wave.

18. The method of claim 15 wherein the coupling medium is Lucite and the coating is metalspray and the first angle is thus about 66 degrees.

19. The method of claim 15 wherein the coated object is a cylinder defining a roll cylindrical surface of a Yankee dryer.

20. The method of claim 19 wherein a transducer is caused to traverse the roll cylindrical surface by rotating the Yankee dryer about an axis defined by the cylindrical surface and moving the transducer along the coated surface of the cylinder parallel to the axis so describing a helical pattern on the cylindrical surface of the dryer.

21. The method of claim 20 wherein circumferential turns of the helical pattern are spaced about one eighth of an inch apart.

22. The method of claim 20 wherein the traverse over the coated dryer surface is recorded for a substantial portion of the traverse of the coated surface.

* * * * *